United States Patent [19]
Carter

[11] Patent Number: 6,004,301
[45] Date of Patent: Dec. 21, 1999

[54] SURFACE ACCESS DOUBLE HEMOSTATIC VALVE FOR HEMODIALYSIS

[76] Inventor: Bruce C. Carter, 4034 Copeland Rd., Tyler, Tex. 75701

[21] Appl. No.: 09/026,378

[22] Filed: Feb. 19, 1998

[51] Int. Cl.[6] .................................................. A61M 5/00
[52] U.S. Cl. ............................................. 604/256; 604/93
[58] Field of Search ............................. 604/93, 256, 246, 604/247, 4, 264, 280

[56] References Cited

U.S. PATENT DOCUMENTS

| | | | |
|---|---|---|---|
| 4,832,054 | 5/1989 | Bark | 128/899 |
| 4,929,235 | 5/1990 | Merry et al. | 604/167 |
| 5,702,363 | 12/1997 | Flaherty | 604/93 |
| 5,741,228 | 4/1998 | Lambrecht et al. | 604/93 |

*Primary Examiner*—Wynn Wood Coggins
*Assistant Examiner*—Deborah Blyveis
*Attorney, Agent, or Firm*—Michael A. O'Neil

[57] ABSTRACT

A surface access double hemostatic valve comprises a first hemostatic valve mounted in the wall of a hemodialysis graft, a chamber extending from the first hemostatic valve, and a second hemostatic valve mounted at the distal end of the chamber for positioning at the surface of the skin of the patient. The graft having the surface access double hemostatic valve mounted thereon is surgically installed in the skin of the patient. Thereafter the interior of the chamber is sterilized and a blood access member is inserted through the second hemostatic valve, through the chamber, through the second hemostatic valve, and into the interior of the graft for access to blood flowing therethrough to effect hemodialysis.

1 Claim, 9 Drawing Sheets

SURFACE ACCESS DOUBLE HEMOSTATIC VALVE FOR HEMODIALYSIS

BACKGROUND AND SUMMARY OF THE INVENTION

Modern hemodialysis techniques include the surgical installation of one or more hemodialysis grafts to facilitate access to the blood flow of the patient. Currently hemodialysis patients undergo repetitive, often painful large needle punctures of their skin and underlying tissue numerous times per week to gain entry into the hemodialysis grafts. The disadvantages of this approach are numerous and well documented. Hematomas can result from uncontrolled bleeding. The graft is damaged by the multiple puncture technique leading ultimately to poor and inadequate functioning or thrombosis resulting in the need for additional operations, replacement of the graft and resultant tissue trauma. Temporary dialysis access through internal jugular veins or other venous access site further adds to patient morbidity.

Significant technical expertise and nursing care is currently required to puncture the grafts. Following dialysis and needle removal, skilled nursing staff are required to hold pressure on the graft puncture site for variable periods of time which not infrequently last up to an hour.

The present invention comprises a surface access double hemostatic valve for hemodialysis which overcomes the foregoing and other problems long since associated with the prior art. In accordance with the broader aspects of the invention, a surface access double hemostatic valve includes a first valve which is secured in the wall of a hemodialysis graft. A chamber extends from the first hemostatic valve to a second hemostatic valve which is situated at the outer surface of the skin of the patient. Access to the blood flow of the patient is achieved by inserting an instrument through the second hemostatic valve, through the chamber, through the first hemostatic valve, and into the graft.

The advantages obtained by means of the invention include the following:

1. Decreased patient suffering.
2. Increased patient comfort and satisfaction.
3. No needle damage to the hemodialysis graft.
4. Longer lifetime of the graft.
5. Decreased number of surgical procedures in the lifetime of the patient.
6. Decreased cost of medical care for hemodialysis.
7. Improved graft functioning with greater flow rates and decreased time in dialysis.
8. Decreased nursing staff time without difficult, highly skilled punctures having to be performed.
9. Decreased post-procedure time with no requirement for applying pressure at the puncture site to control bleeding.
10. Further potential for improving graft design by strengthening the material used as graft punctures are no longer required.
11. Decreased number of graft-related complications for patients undergoing long-term dialysis with less arm hematomas (therefore less associated vein, nerve, and arterial compression with less deep venous thrombosis and decreased potential for decreased use of the extremity), less potential for arterial embolic disease and, less exposure to the risks of anesthesia with decreased need for surgical intervention or radiologic declot intervention.
12. Decreased damage to the entire venous system of the patient with decreased need for temporary access to other large caliber veins because of graft malfunction.

BRIEF DESCRIPTION OF THE DRAWINGS

A more complete understanding of the invention may be had by reference to the following Detailed Description when taken in conjunction with the accompanying Drawings, wherein.

DETAILED DESCRIPTION

Figure 1:
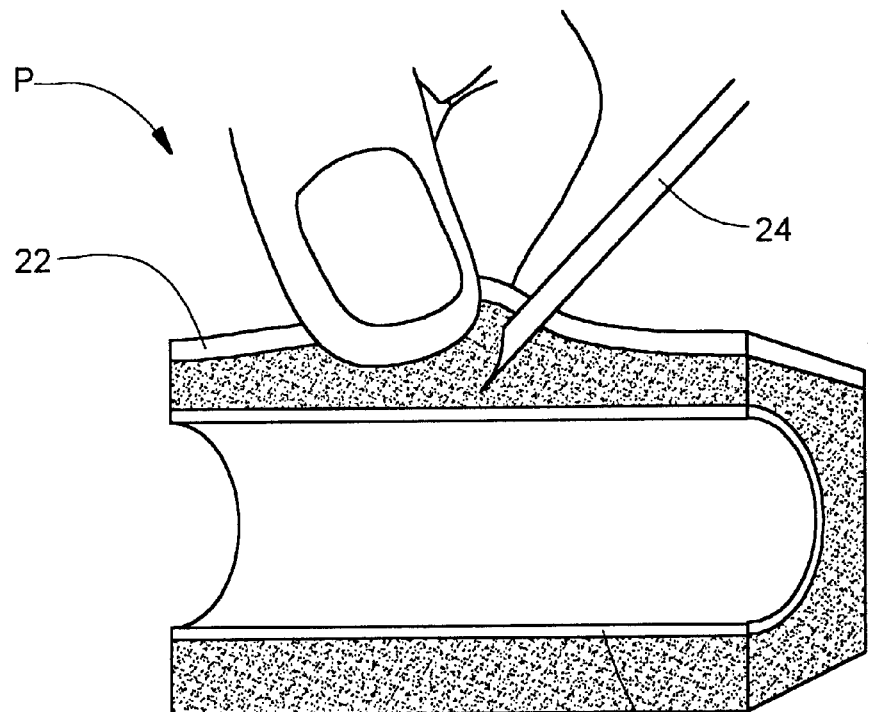
FIG. 1 is a diagrammatic illustration of an initial step of a prior art technique for gaining access to a hemodialysis graft in order to effect hemodialysis.

Referring now to the Drawings, and particularly to FIGS. 1, 2, 3, and 4 thereof, there is illustrated a currently utilized hemodialysis technique. In accordance with current practice, a hemodialysis graft 20 is installed beneath the skin 22 of a patient P. The graft 20 is connected either to an artery or a vein of the patient and is utilized to provide access to the blood flow of the patient during the dialysis procedure.

Figure 2:
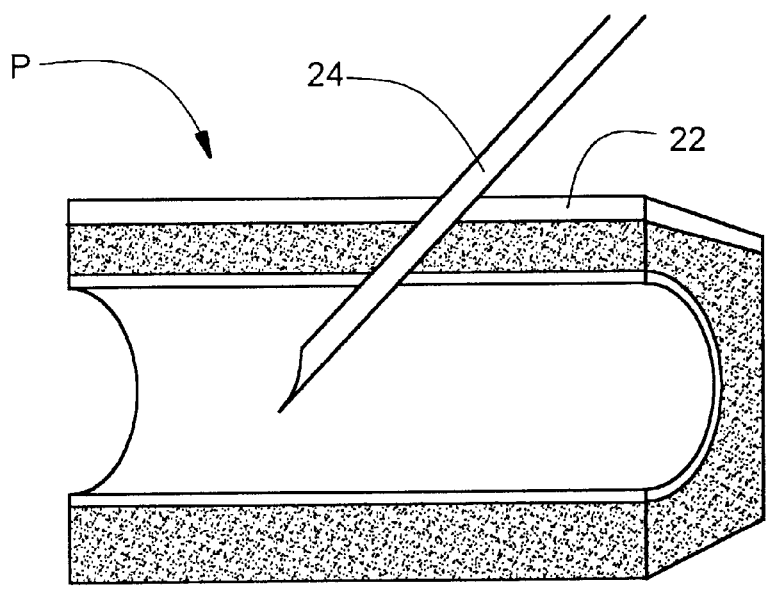
FIG. 2 is a diagrammatic illustration of a subsequent step in the technique of FIG. 1.

The skin 22 of the patient P is first "tented" as illustrated in FIG. 1, and a needle 24 is inserted therethrough. The needle 24 is preferably inserted through the skin 22 of the patient P at an angle of 45°. As is illustrated in FIG. 2, further insertion of the needle 24 causes the needle to penetrate the graft 20, again at an angle of 45°. As will be understood by reference to FIGS. 1 and 2, the needle 24 is inserted through the skin 22 and the graft 20 with the tip thereof pointed down. Following insertion of the needle through the graft, the needle is rotated 180° so that the tip thereof is pointed up.

Figure 3:
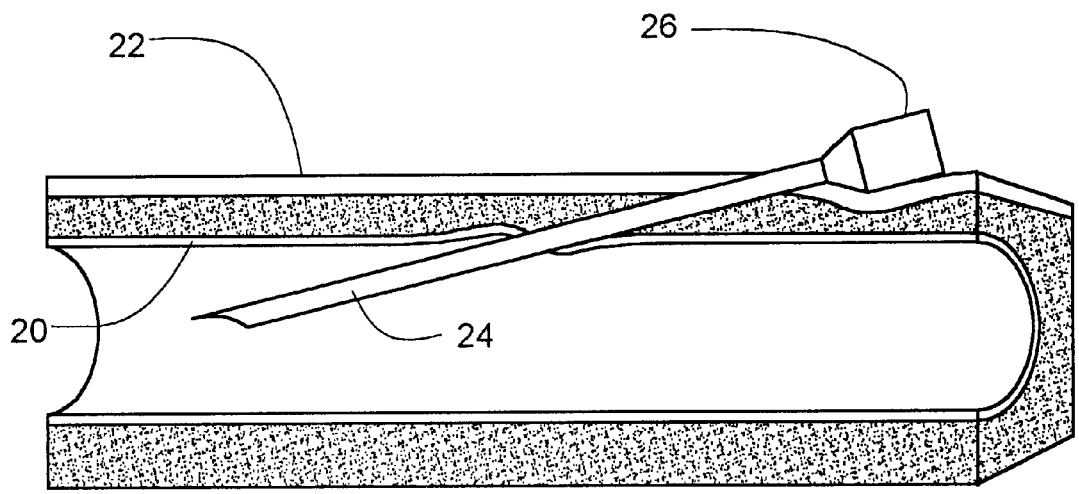
FIG. 3 is a diagrammatic illustration of a still later step in the technique of FIG. 1.

Insertion of the needle continues until the hub 26 of the needle 24 engages the skin 22 of the patient P as illustrated in FIG. 3.

Figure 4:
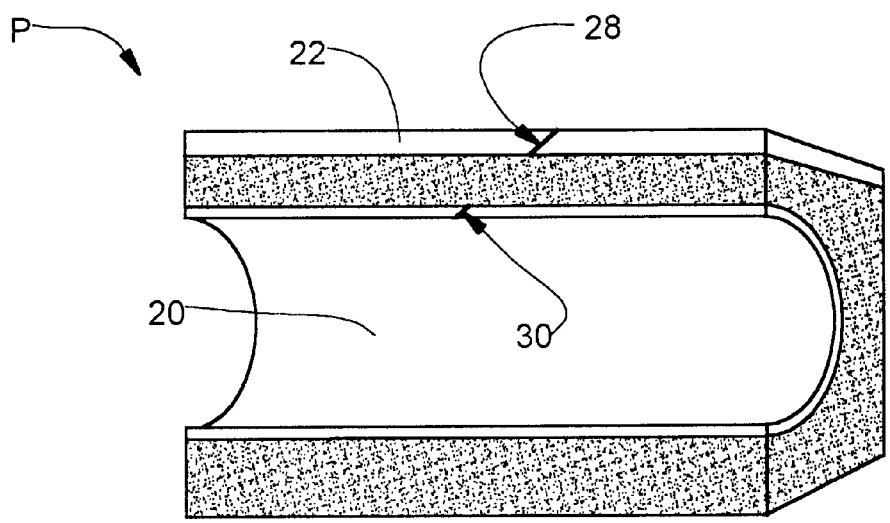
FIG. 4 is a diagrammatic illustration of the successful completion of the technique of FIG. 1.

When the needle 24 has been inserted as illustrated in FIG. 3, the hemodialysis procedure begins and continues for a predetermined period of time as prescribed by the attending physician. When the hemodialysis procedure is complete, the needle 24 is withdrawn from the graft 20 and the skin 22 in the usual manner. Assuming that the needle 24 has been properly inserted through the skin 22 and the graft 20, the point of penetration through the skin 28 and point of penetration through the graft 30 will be misaligned following withdrawal of the needle as illustrated in FIG. 4. This is advantageous in reducing the possibility of bleeding through the graft and the skin following the hemodialysis procedure. Nevertheless it is frequently necessary to maintain pressure on the point of the skin 28 to avoid bleeding.

Figure 5:
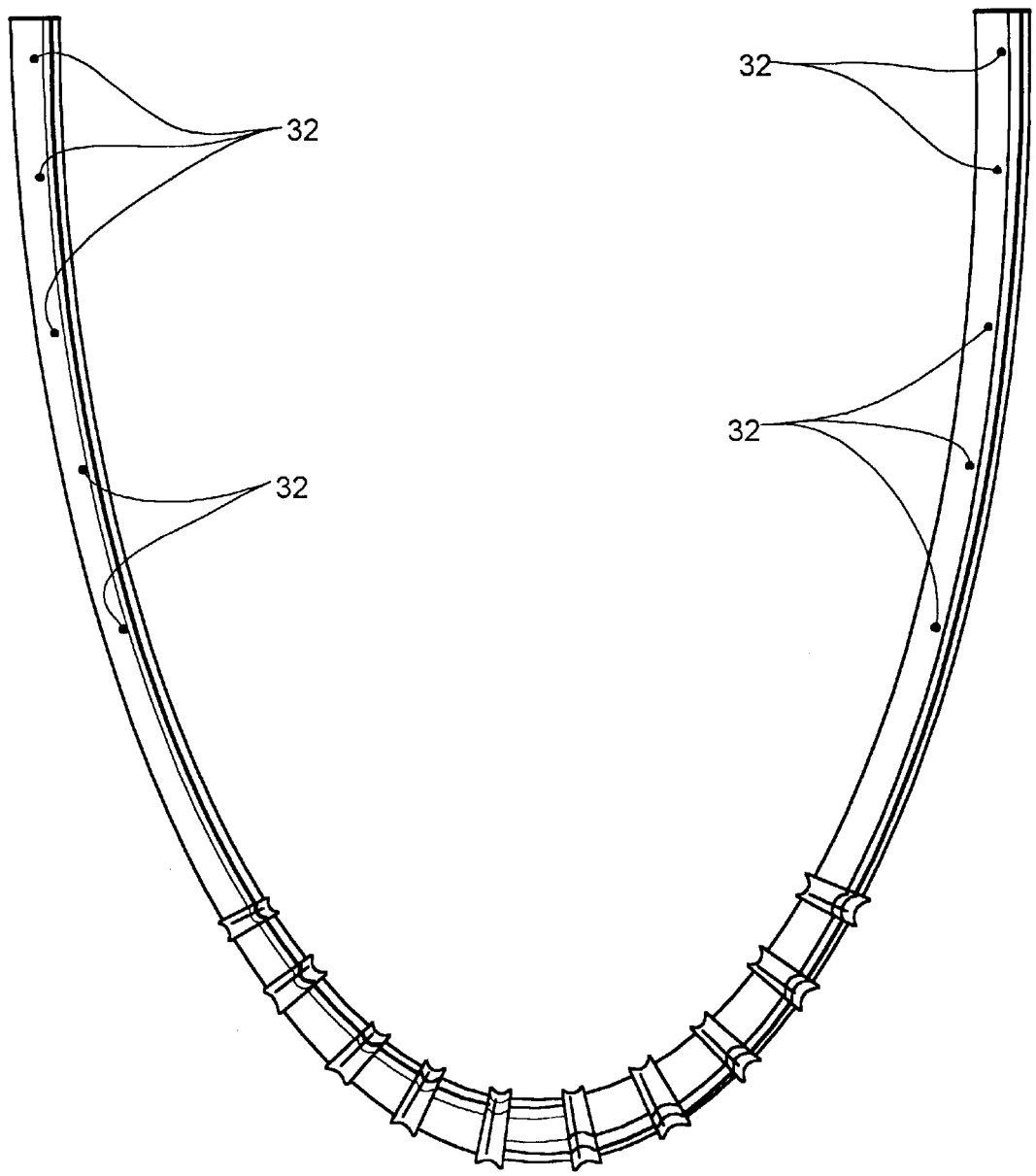
FIG. 5 is an illustration of a hemodialysis graft.

Referring to FIG. 5, the graft 20 is illustrated in further detail. In FIG. 5 the graft 20 is provided with a plurality of hypothetical reference points 32 each located one centimeter from the next adjacent reference point. As is suggested by the reference points 32, in the practice of the currently used hemodialysis technique, the needle is not inserted at the same location preparatory to successive dialysis procedures. Instead, the sites of successive needle penetrations into the graft 20 are separated by at least one centimeter. This is to reduce the possibility of pseudoaneurysm at the needle insertion site, and also to reduce the possibility of early graft failure.

As will perhaps be apparent from the foregoing brief discussion from currently used hemodialysis techniques, the state of the art is characterized by patient dissatisfaction, discomfort, and suffering due to the necessity of frequent needle insertions through the skin of the patient. A parallel problem is reduction of the anticipated life of the hemodialysis graft due to repeated needle insertions therethrough. This leads to an increased number of surgical procedures over the lifetime of the patient in order to replace failed grafts which in turn leads to significant increases in the cost of treatment. Thus, a need exists for improvements in the art and practice of hemodialysis with a view toward significant reductions in the foregoing problems.

Figure 6:
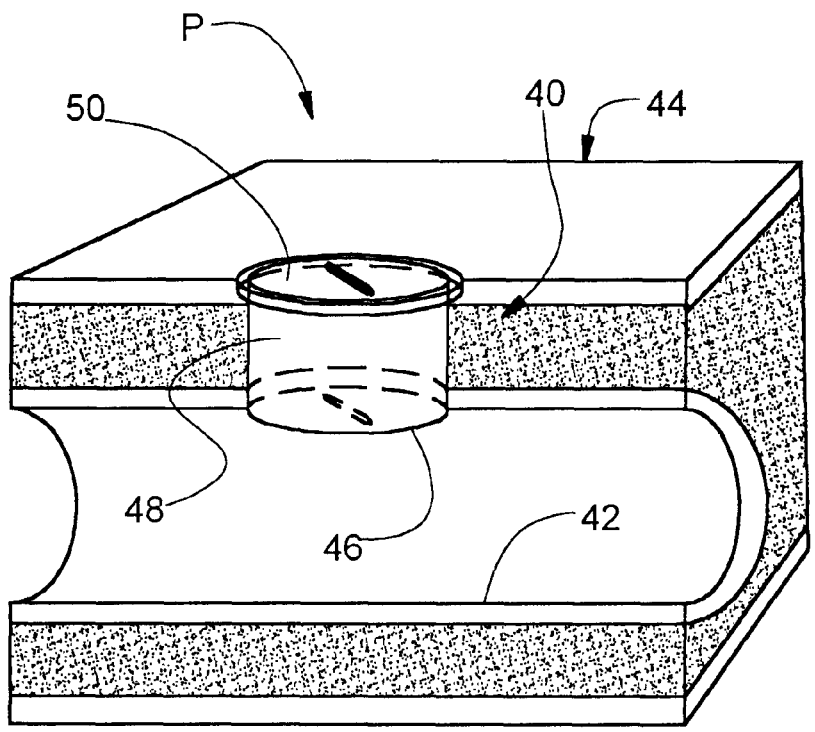
FIG. 6 is a diagrammatic illustration of an apparatus and method comprising a first embodiment of the present invention.

Referring now to FIG. 6, there is shown a surface access double hemostatic valve 40 comprising the present invention. In accordance with the invention, an otherwise conventional hemodialysis graft 42 is inserted beneath the skin 44 of a patient P utilizing conventional surgical techniques. A first hemostatic valve 46 is secured in the wall of the graft 42. A chamber 48 extends outwardly from the hemostatic valve 46 through the skin 44 of the patient P. A second hemostatic valve 50 is located at the distal end of the chamber 48 and is mounted parallel to the surface of the skin 44 of the patient. As will be understood by those skilled in the art, the use of the present invention facilitates access to the interior of the graft 42 through the double hemostatic valve 40 without requiring the insertion of needles through the skin 44 and the graft 42.

Figure 7:
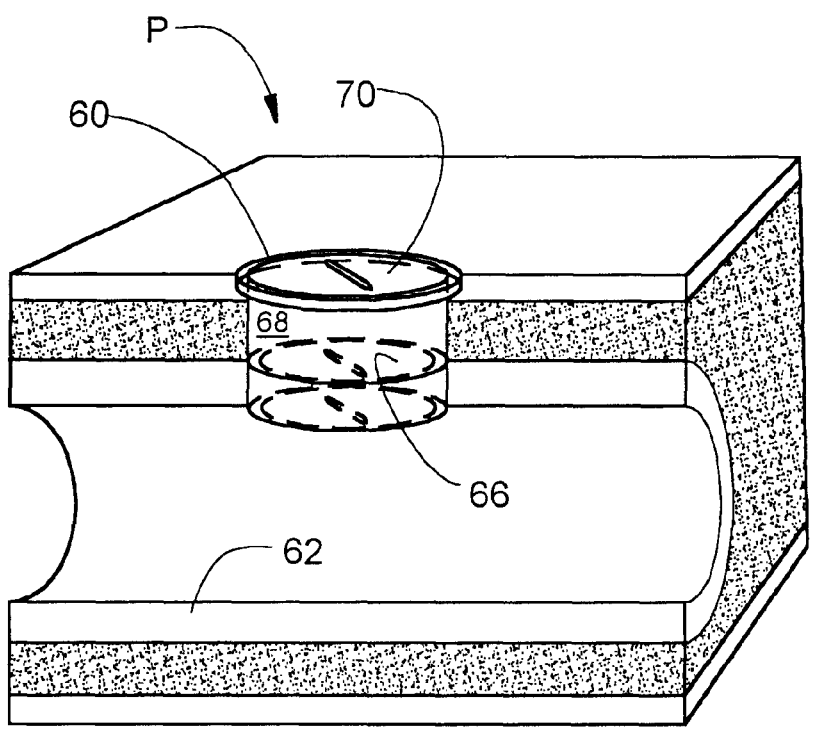
FIG. 7 is a detailed illustration of an apparatus and method comprising a second embodiment of the present invention.
Figure 8:
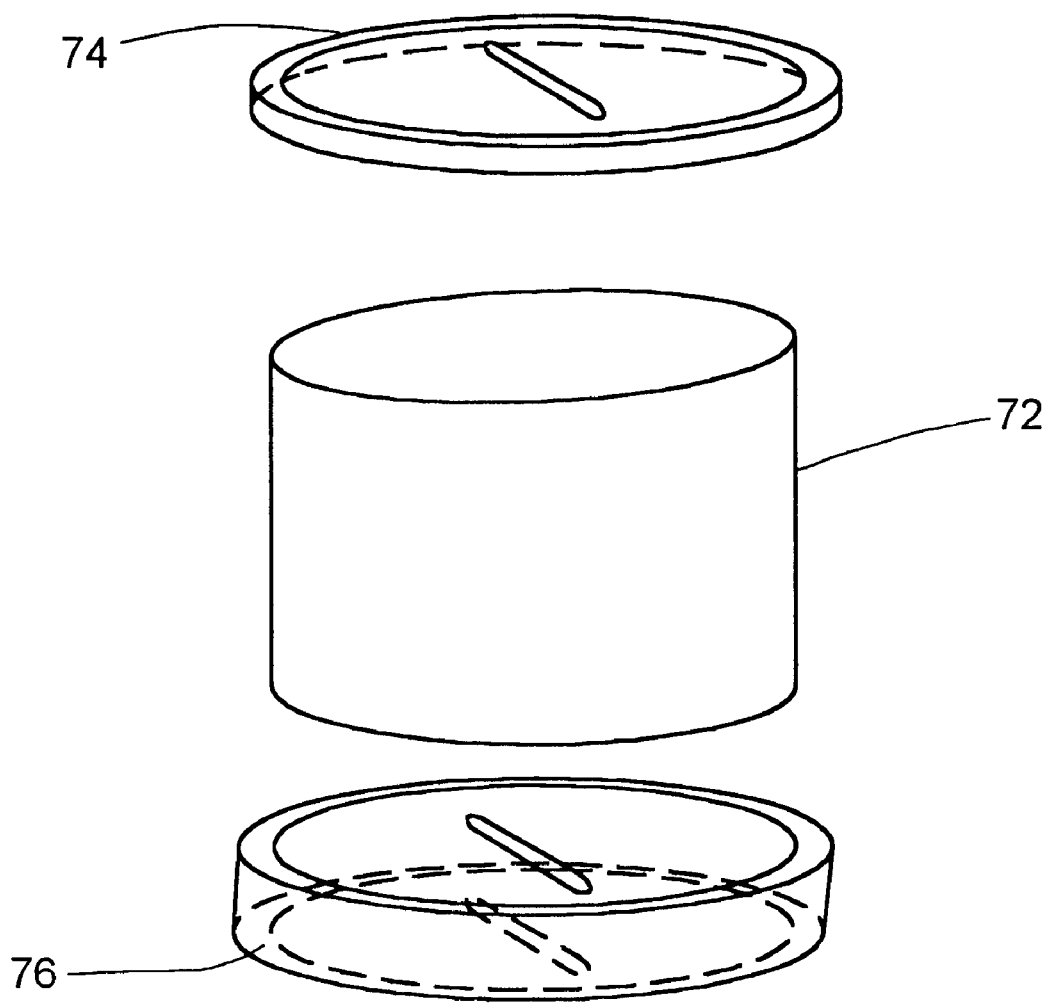
FIG. 8 is an exploded view further illustrating the method and apparatus of FIG. 7.

FIGS. 7 and 8 illustrate a second embodiment of the invention. Again, a double hemostatic valve 60 is secured to a hemodialysis graft 62 and extends therefrom to the surface of the skin 64 of the patient P. The valve 60 includes a first hemostatic valve 66 secured in the graft 62, a chamber 68 extending from the valve 66, and a second hemostatic valve 70 located at the surface of the skin of the patient P.

As is best illustrated in FIG. 8, the valve 60 of FIG. 7 differs from the valve 40 of FIG. 6 in that the valve 66 of the double hemostatic valve 60 comprises a double thickness hemostatic valve 72 mounted between two wafers 74 and 76. The wafers 74 and 76 are preferably mounted within the wall of the graft 62 and comprise either a suitable metal, such as stainless steel, or a suitable plastic material.

Figure 9:
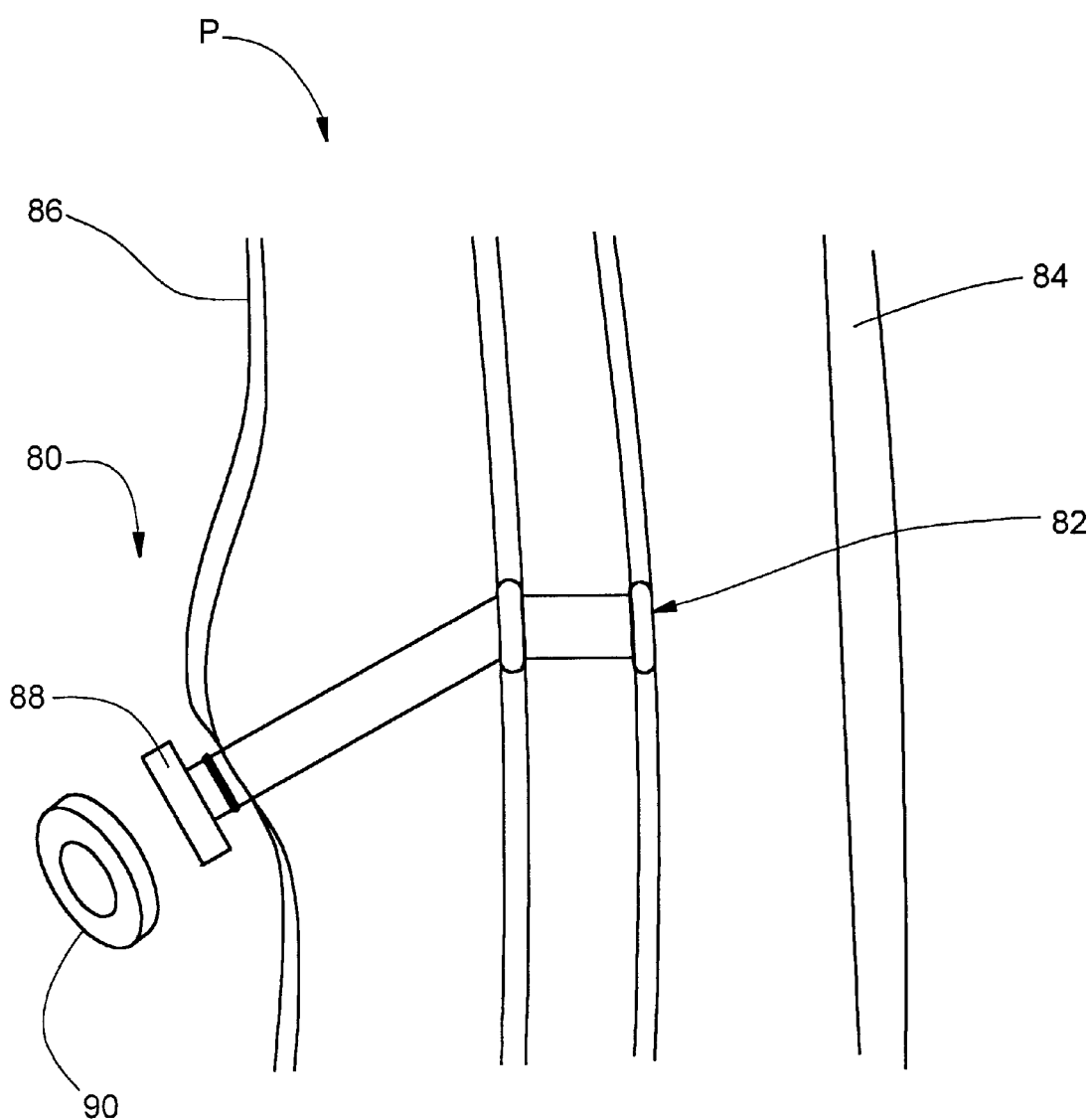
FIG. 9 is a further illustration of the method and apparatus of the present invention.

Referring to FIG. 9, there is shown a surface access double hemostatic valve 80 comprising the present invention. The valve 80 may be constructed similarly to the valve 40 of FIG. 6 or to the valve 60 of FIGS. 7 and 8 and includes a first hemostatic valve 82 secured in the wall of a hemodialysis graft 84 installed beneath the surface of the skin 86 of a patient P. The valve 80 further includes a second hemostatic valve 88 located at the surface of the skin of the patient P to provide access to the interior of the graft 84. A sealing cap 90 is provided for secure engagement with the valve 88 and is normally retained in engagement with the valve except during actual hemodialysis procedures. The purpose of the sealing cap 90 is to prevent contamination of the surface access double hemostatic valve 80 by contact with foreign agents.

Figure 10:
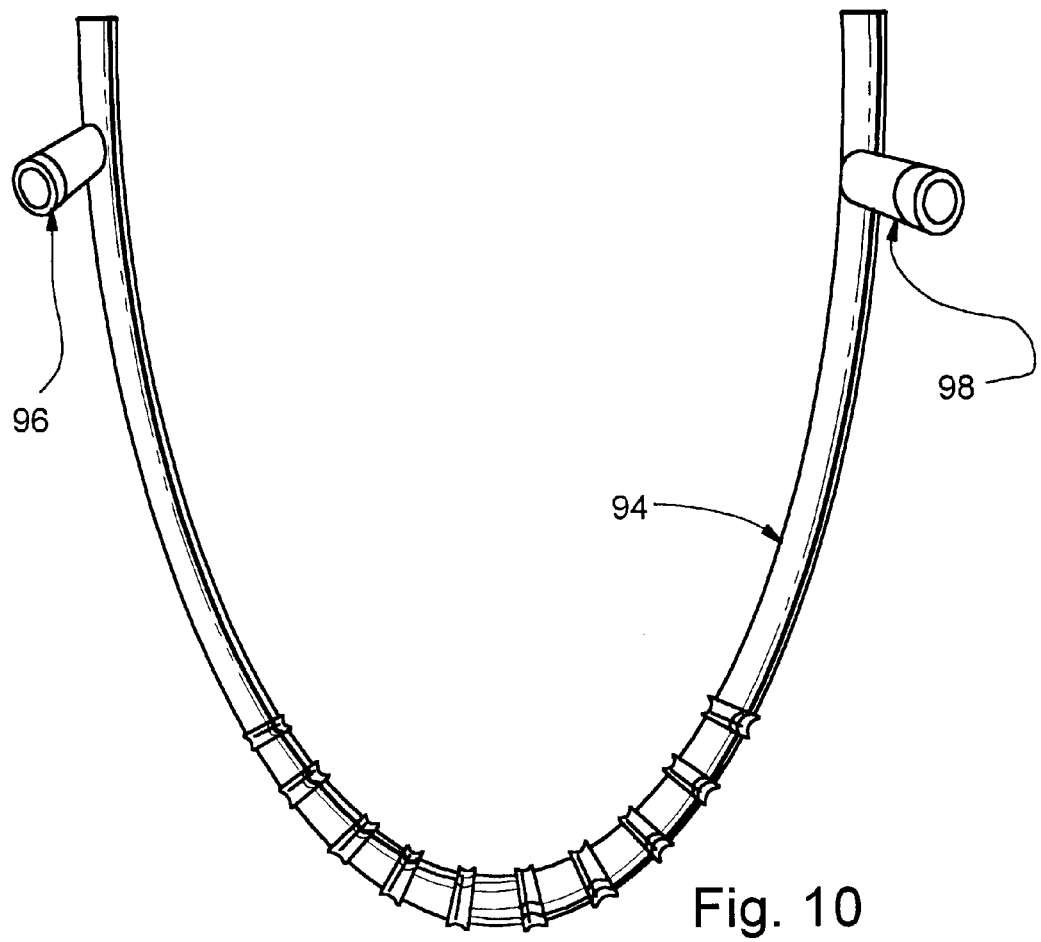
FIG. 10 is an illustration of a hemodialysis graft equipped with the apparatus of the present invention.

FIG. 10 illustrates a hemodialysis graft 94 having surface access double hemostatic valves 96 and 98 mounted thereon at spaced apart locations. The valves 96 and 98 may be constructed similarly to the valve 40 illustrated in FIG. 6. Alternatively, the valves 96 and 98 may be constructed similarly to the valves 60 illustrated in FIGS. 7 and 8. In either case, the valves 96 and 98 may be provided with sealing caps of the type illustrated in FIG. 9.

Figure 11:
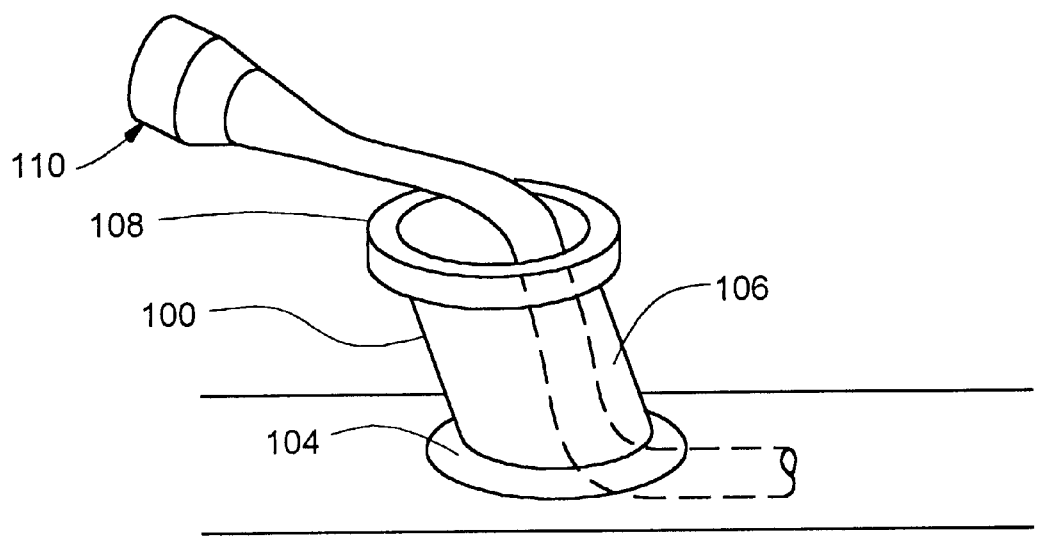
FIG. 11 is a further illustration of the method of the present invention.

Referring now to FIG. 11, there is shown a surface access double hemostatic valve 100 incorporating the present invention. The valve 100 is utilized in conjunction with an otherwise conventional hemodialysis graft 102 and may be constructed similarly to the valve 40 of FIG. 6, or the valve 60 of FIGS. 7 and 8, or the valve 80 of FIG. 9. As will be appreciated by reference to the foregoing FIGURES, the valve 100 includes a first hemostatic valve 104 which is secured in the wall of the graft 102, a chamber 106 extending from the valve 104, and a second hemostatic valve 108 located at the surface of the skin of the patient.

After the graft 102 and the valve 100 have been installed, the interior of the chamber 106 is flushed with a heparinized saline solution. Thereafter, an introducer set sheath 110 is inserted through the valve 108, the chamber 106, and the valve 104 and into the interior of the graft 102. By this means, access to the blood of the patient flowing through the interior of the graft 102 is provided without the necessity of penetrating the skin of the patient and the graft located therein with a needle.

Figure 12:
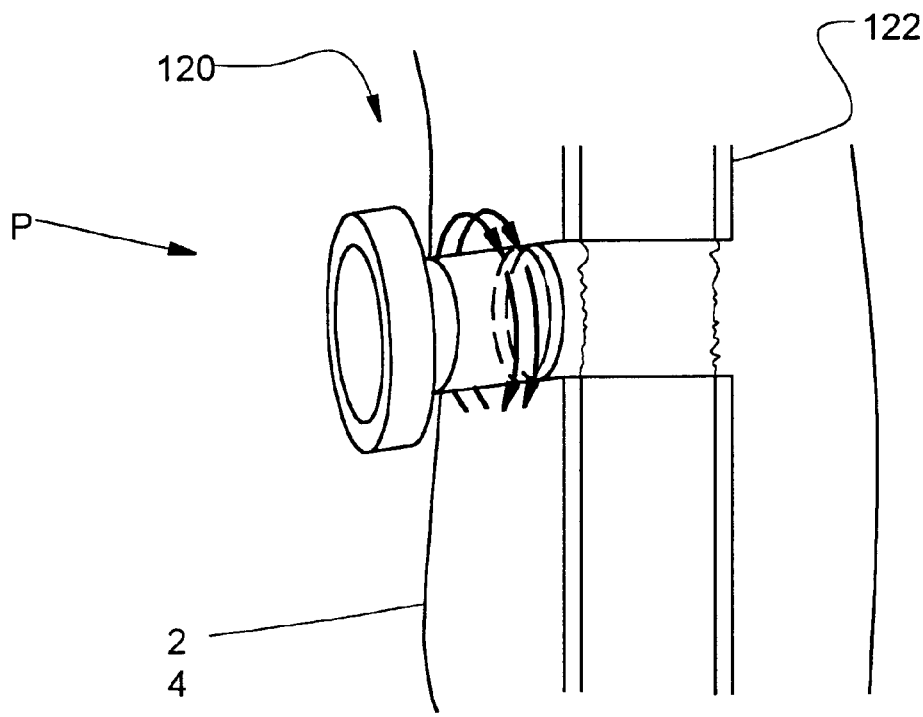
FIG. 12 is an illustration of a first step in an alternative method according to the present invention.
Figure 13:
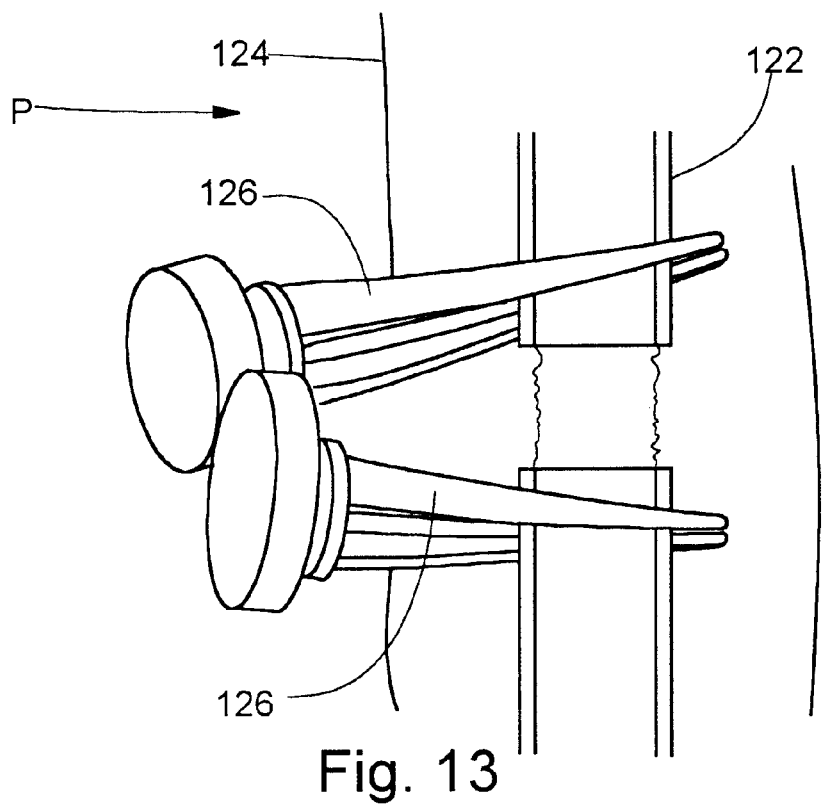
FIG. 13 is an illustration of a later step in the alternative method of the present invention.
Figure 14:
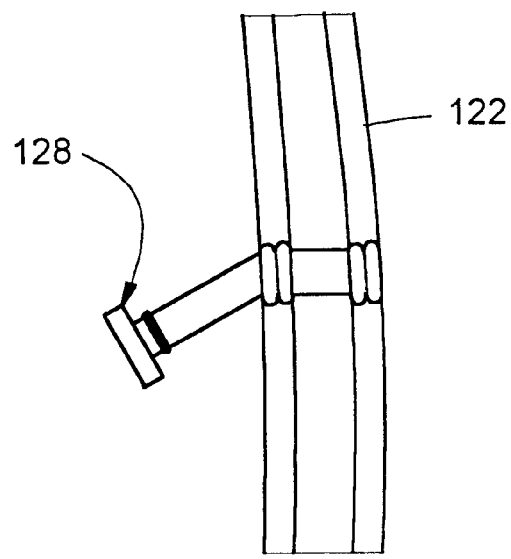
FIG. 14 is an illustration of the completion of the alternative method of the present invention.

FIGS. 12, 13, and 14 illustrate an aspect of the present invention which facilitates the replacement of the surface access double hemostatic valve of the present invention utilizing simple local anesthetic based techniques. FIG. 12 illustrates a surface access double hemostatic valve 120 which for whatever reason requires replacement. The valve 120 is secured to and mounted in fluid communication with a graft 122 which has previously been installed beneath the surface of the skin 124 of a patient P utilizing conventional surgical techniques. To accomplish replacement of the valve 120, a local anesthetic is administered to the patient P again utilizing conventional techniques. Thereafter, the graft 122 is sealed utilizing temporary clamps 126, and the valve 120 is removed. Thereafter a new lock-in double hemostatic valve 128 is secured in the wall of the graft 122 and the clamps 126 are removed. At this point the valve 128 and the graft 122 are arranged as illustrated in FIG. 14. The use of the valve 128 is the same as described hereinabove in conjunction with the valves 40, 60, and 80.

Figure 15:
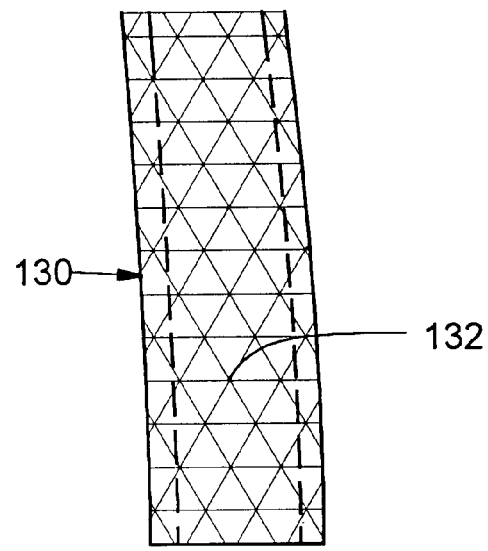
FIG. 15 is a diagrammatic illustration of a first improved hemodialysis graft according to the present invention.
Figure 16:
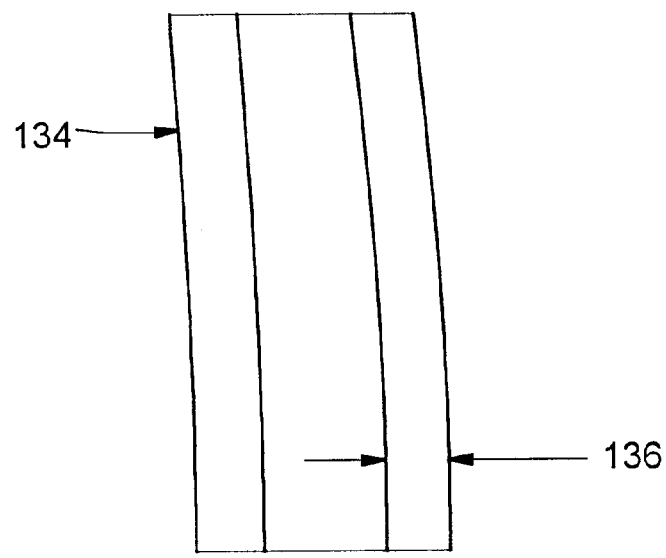
FIG. 16 is a diagrammatic illustration of a second improved hemodialysis graft according to the present invention.

FIGS. 15 and 16 illustrate alternative hemodialysis graft designs which may be utilized in the practice of the invention. In FIG. 15, an otherwise conventional hemodialysis graft 130 is reinforced by a metal stent 132. In FIG. 16 there is illustrated an otherwise conventional hemodialysis graft 134 having a substantially increased wall thickness 136. As will be appreciated by those skilled in the art, hemodialysis grafts having reinforced and/or extra thick walls cannot be used in the practice of conventional hemodialysis techniques due to the inherent difficulty of inserting a needle therethrough. Conversely, such improved hemodialysis designs are readily adapted to the practice of the present invention which does not require the insertion of a needle through the wall of the graft.

Although preferred embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention.

I claim:

1. For use in the practice of hemodialysis, a surface access double hemostatic valve comprising;

an elongate annular wall comprising a hemodialysis graft;

a first hemostatic valve mounted in the wall of the graft;

a chamber surrounding the first hemostatic valve and extending outwardly therefrom to a distal end; and a second hemostatic valve mounted at the distal end of the chamber for positioning at the surface of the skin of the patient having the hemostatic valve installed therein:

the second hemostatic valve comprising comprising a single thickness hemostatic valve;

the first hemostatic valve comprising a double thickness hemostatic valve; and wafers mounted on opposite sides of the first hemostatic valve.

* * * * *